US012465477B2

(12) United States Patent
Pasquino et al.

(10) Patent No.: US 12,465,477 B2
(45) Date of Patent: Nov. 11, 2025

(54) TRANSCATHETER ANTI EMBOLIC FILTER FOR ARTERIAL AND VENOUS VESSELS

(71) Applicant: AorticLab Srl, Colleretto Giacosa (IT)

(72) Inventors: Enrico Pasquino, Savigny (CH); Franco Osta, Mombello Monferrato (IT); Stefano Osta, Saluggia (IT); Yi Peng Bai, Milan (IT); Giulia Parigi, Milan (IT); Francesco Bonetti, Turin (IT)

(73) Assignee: AORTICLAB SRL, Colleretto Giacosa (IT)

( * ) Notice: Subject to any disclaimer, the term of this patent is extended or adjusted under 35 U.S.C. 154(b) by 603 days.

(21) Appl. No.: 17/442,168

(22) PCT Filed: Apr. 3, 2020

(86) PCT No.: PCT/EP2020/059601
§ 371 (c)(1),
(2) Date: Sep. 23, 2021

(87) PCT Pub. No.: WO2020/201524
PCT Pub. Date: Oct. 8, 2020

(65) Prior Publication Data

US 2022/0168087 A1 Jun. 2, 2022

(30) Foreign Application Priority Data

Apr. 5, 2019 (EP) .................................... 19167599

(51) Int. Cl.
*A61F 2/01* (2006.01)

(52) U.S. Cl.
CPC ............ *A61F 2/0105* (2020.05); *A61F 2/013* (2013.01); *A61F 2002/016* (2013.01)

(58) Field of Classification Search
CPC .. A61F 2/0105; A61F 2/013; A61F 2002/016; A61F 2002/015;
(Continued)

(56) References Cited

U.S. PATENT DOCUMENTS 6,361,545 B1 3/2002 Macoviak et al.
7,749,245 B2 7/2010 Cohn et al.
(Continued)

FOREIGN PATENT DOCUMENTS

AU 2011202667 A1 6/2011
JP 2010517642 A 5/2010
(Continued)

OTHER PUBLICATIONS

Office Action, issued in Japanese Patent Application No. 2021-557526 dated Nov. 21, 2023.
(Continued)

*Primary Examiner* — Brooke Labranche
(74) *Attorney, Agent, or Firm* — NIXON & VANDERHYE

(57) ABSTRACT

An intra-vessel transcatheter filter device (1) designed to capture and remove emboli, thus preventing distal embolization, comprising: • a tubular filter (2) comprising a flexible porous material and defined by a distal element and a proximal element, namely a main body (3) and a funnel (4); i. said main body (3) having a length adapted to extend within a suitable vessel zone; said main body (3) comprising: a) a distal end (5) that is adapted to be radially coupled with said zone and hermetically sealed to it when the device is in an active configuration, said distal end (5) being provided of selectively actionable closure means so that said distal end is designed to be open when the device is in an active configuration and closed before the device retraction, b) a proximal end (6); ii. said funnel (4) forming an
(Continued)

extension of said main body (3), with the funnel base located at said proximal end (6). • a support structure assembly (8) comprising: i. a supporting catheter (11) extending within said main body (3), ii. one radially expandable distal structure (9) fixed to said distal end (5), iii. one radially expandable proximal structure (10) positioned in correspondence of said proximal end (6), said distal structure (9) and said proximal structure (10) being fixed at least in an end to said supporting catheter (11).

19 Claims, 25 Drawing Sheets

(58) Field of Classification Search
CPC ...... A61F 2002/9511; A61F 2002/9534; A61F 2220/0075; A61F 2230/0067
See application file for complete search history.

(56) References Cited

U.S. PATENT DOCUMENTS

| | | | |
|---|---|---|---|
| 10,213,227 | B2 | 2/2019 | Pain et al. |
| 10,568,729 | B2 | 2/2020 | Pain et al. |
| 2002/0095116 | A1 | 7/2002 | Strecter |
| 2005/0015112 | A1 | 1/2005 | Cohn et al. |
| 2007/0067021 | A1 | 3/2007 | Haverkost et al. |
| 2008/0269877 | A1 | 10/2008 | Jenson et al. |
| 2010/0312268 | A1 | 12/2010 | Belson |
| 2012/0035721 | A1 | 2/2012 | Vesely |
| 2014/0005540 | A1 | 1/2014 | Merhi |
| 2015/0202038 | A1 | 7/2015 | Krahbichler |
| 2015/0342602 | A1 | 12/2015 | Jimenez et al. |
| 2015/0342717 | A1 | 12/2015 | O'donnell et al. |
| 2016/0235515 | A1 | 8/2016 | Merhi |
| 2017/0042659 | A1 | 2/2017 | Russell et al. |
| 2017/0119517 | A1 | 5/2017 | Pain et al. |
| 2018/0110607 | A1 | 4/2018 | Russell et al. |
| 2018/0177582 | A1 | 6/2018 | Lashinski |
| 2019/0000604 | A1 | 1/2019 | Eli |
| 2020/0006942 | A1 | 1/2020 | Lansing, Jr. et al. |
| 2020/0197033 | A1 | 6/2020 | Pasquino et al. |
| 2022/0387063 | A1 | 12/2022 | Jenson et al. |

FOREIGN PATENT DOCUMENTS

| | | | |
|---|---|---|---|
| JP | 2015506227 | A | 3/2015 |
| JP | 2018526153 | A | 9/2018 |
| JP | 2019501712 | A | 1/2019 |
| WO | 0044313 | A1 | 8/2000 |
| WO | 2015184450 | A1 | 12/2015 |
| WO | 2015185870 | A1 | 12/2015 |
| WO | 2017042808 | A1 | 3/2017 |
| WO | 2018211344 | A1 | 11/2018 |
| WO | 2020151995 | A1 | 7/2020 |
| WO | 2020201524 | A1 | 10/2020 |

OTHER PUBLICATIONS

International Search Report mailed on Jun. 9, 2020 for Application N° PCT/EP2020/059601.
Written Opinion of the ISA mailed on Jun. 9, 2020 for Application N° PCT/EP2020/059601.

TRANSCATHETER ANTI EMBOLIC FILTER FOR ARTERIAL AND VENOUS VESSELS

CROSS REFERENCE TO RELATED APPLICATIONS

The present application is a United States national stage application of international patent application with the Serial No. PCT/EP2020/059601 filed on Apr. 3, 2020, designating the United States, and claims foreign priority to European patent application with the Serial No. EP 19167599.0 that was filed on Apr. 5, 2019, the contents of both these document herewith incorporated by reference in their entirety.

FIELD OF INVENTION

The present invention generally relates to a transcatheter anti embolic filter, in particular to an intra-aortic filter to be used to protect cerebral and peripheral vessels from potential dissemination of emboli.

BACKGROUND OF THE INVENTION

The clinical complications related to the implant of a transcatheter heart valve prosthesis (TAVI) are mainly related to the fact that it overlaps the diseased native valve. The heavy presence of tissue calcifications, involving the valve apparatus and the surrounding tissues, influences the correct deployment of the prosthesis creating the conditions for embolic episodes.

The procedural embolic events, so called “macro-embolic cerebral events”, are occurring during a TAVI implant procedure (during predilation, implant or postdilation) and are mainly related to the embolization of macro debris of calcium of fibroelatic particles usually targeting the brain (strokes), the coronary arteries or the peripheral organs. However, the strokes are the most frightful clinical events occurring, nowadays, at a rate of 2.7% against a rate of 3.3% of the previous generations of TAVIs. This reduction of strokes is related to the minor need of pre- and postdilation during TAVI implant nevertheless this data are unclear since are referring to aortic valves with a mild level of calcification. The post-procedural micro-embolic cerebral events are documented in at least 8% of the patients submitted to investigation. The high incidence of new cerebral lesions after TAVI warrants for a longer-term evaluation of neurocognitive function.

In this study conducted over a short-term follow-up period of 3 months, no impairment of neurocognitive function was observed clinically, and the majority of lesions (80%) had resolved on 3-months MRI. However, the issue of periprocedural brain embolization and its potential effects on neurocognitive function may portend greater clinical implications once the indication for TAVI is broadened to include younger patients with long life expectancy.

Future research in the field of TAVI should thus be directed at developing strategies to reduce the risk of embolization (e.g., less traumatic, smaller-bore catheter systems, improved identification of patients at risk for embolization and a potential use of cerebral protection devices).

In some clinical studies at least 10% of the patients, submitted to TAVI implant, show a neurological damage detectable during psychometric tests. While this occurrence rate can be acceptable in high risk and an old patient population it appears unacceptable in lower-risk younger patients. Several clinical studies are ongoing to better investigate this clinical condition.

Another kind of embolic events are the sub-acute and chronic microembolic events occurring after the immediate post-procedural time. The native aortic calcific valve is rough, with a warty surface, immobilized acting like an atherosclerotic ulcerated plaque. This condition is favoring the formation of microtrombi that later-on embolize towards the brain and other peripheral organs. The native aortic valve left in place as a source of microemboli has been taken into account in several clinical studies that demonstrated their role in the onset of vascular origin dementia. This evidence creates a concern when the TAVI are implanted in younger patients where an acceleration of the vascular dementia could impact in a serious way on the social costs.

In summary the periprocedural clinical complications following a TAVI implant are strongly related to the presence of the heavily calcified aortic valve left in place. It brings, acutely, an occurrence of macro-embolic cerebral events (strokes) and hemodynamic consequences such as the PVLs resulting in a various severity of aortic valve insufficiency. These unsatisfactory clinical outcomes are closely related to an irregular deployment of the transcatheter valve prostheses in concomitance of highly calcified aortic native valves.

The longer-term clinical complications are characterized by the cerebral micro-embolizations generated by the native aortic valve leaflets' left in place that become a source of emboli responsible for vascular dementia.

The overall rate of clinical complications in TAVI is ranging between 5% and 12%. This occurrence is most probably underestimated because it does not include patients with highly calcified and biscuspid native valves.

These evidences highlight the importance of protecting the peripheral organs, in particular the brain and the heart, against embolizations occurring during TAVIs procedures.

The increasing overall use of TAVI respect to SAVR, and the higher rate of intermediate risk patients implanted with TAVI, both are indicating the convenience of adopting embolic protection to optimize the long-term survival and quality of life of these patients.

AKI (Acute Kidney Injury) is a frequent complication after TAVI being reported in ranges from 8.3% to 58%. Differing results might partially be explained by the use of different definitions of AKI. In general, this complication is correlated to comorbidities, access route (transfemoral, transapical or others) and amount of contrast liquid used during the procedure. There aren't clinical study on the correlation between the embolization process that occurs during the TAVI procedure and AKI, due also to the absence of a device that can capture the emboli direct to the renal zone, but it's possible to think that the cloud of embolization detached from the valve during the procedure can help the occurrence of this complication.

The abovementioned complications associated to TAVI procedures apply also to other transcatheter procedures, such as valvuloplasty (when unassociated to TAVI), native valve repair and heart recovery procedures, all conditions potentially leading to emboli release from ventricle, native valve or thoracic aorta. Furthermore, catheter navigation itself along a calcified aorta, can make calcification dislodgement and emboli release.

Furthermore, emboli complications are shown in transcatheter procedures other than intra-aortic ones, therefore an antiembolic protection can be highly recommended also for other districts.

Actually, patents applications disclosing emboli protection have been filed since a long time, see for instance U.S. Pat. No. 6,361,545 that shows a perfusion filter catheter able to be adopted in the frame of SAVR and cardiopulmonary bypass procedures or Australian patent application AU 2011202667 that discloses and embolic filter apparatus and method for heart valve replacement.

Nowadays, there are only few devices in clinical use that protect cerebral and peripheral circulation on the frame of transcatheter cardiac and aortic procedures.

The deflector devices deflect emboli from the brachiocephalic trunk and the left common carotid artery towards the peripheral circulation: therefore, they only impede debris entering in the cerebral vessels and diverting them to the peripheral circulation. Moreover, in case of dislodgement from their intended position, the diverting function is missed.

The antiembolic filter on the market, whose main characteristics are disclosed in US Patent Application US 2018/177582, actually captures emboli with a mesh, but only cover two of the three cerebral vessels and not the peripheral circulation.

Other Patents, as US Patent Applications US 2014/0005540 and US 2016/0235515 disclose an embolic protection device filter which is able to protect the cerebral and systemic circulation, although they show some difficulties on the interaction with other working catheters, such as the ones bearing TAVI devices, that need to be positioned before the filter deployments; moreover, during the TAVI positioning, being its catheter outside the filter protection, a small area of the aorta results unprotected; finally, in case TAVI repositioning in descending aorta is required, it would be needed to temporary remove the filter protection.

US Patent Application US 2018/0110607 discloses an embolic protection device filter which is able to protect the cerebral and systemic circulation; the device has a collection chamber for emboli captured containment, and allows the passage of other catheters inside its cylindrical body. Some disadvantages are shown by the mesh pore size, whose range is defined in the range of about 1 mm to about 0.1 mm, and by the absence of a distal closure mechanism that inherently would prevent upstream release of emboli at closure.

International patent application WO 2017/042808 discloses an embolic protection device including a distal porous deflector covering cerebral vessels connected to a proximal emboli collector comprising at least one filter pocket able to be crossed. Although the distal deflector can appear advantageous in terms of encumbrance respect to a full filter configuration, it actually shows disadvantages when interacting with other working catheters, which can result in a loss of cerebral protection in case of small deflector movements.

International patent applications WO 2015/185870 and WO 2018/211344 both disclose a filter device, including a temporary valve prosthesis, designed to be inserted in aorta. Both devices provide improvements with respect to other prior art devices. They however show some drawbacks, such as their positioning proximal respect to the native valve, that limits the possibility to directly operate onto it, and the difficulty to insert additional devices through the prosthesis due to catheter dimensional constraints.

SUMMARY OF THE INVENTION

The occurrence of clinical events, as discussed in the previous chapter, are prevented with the device of the present invention, as defined in the claims.

The device according to the invention includes an antiembolic filter comprising a proximal funnel that allows working catheters crossing a generally closed filter port, whilst preventing downstream collected emboli release; this allows the working catheters of accessories and/or transcatheter devices be tracked inside the filter without directly contacting the vessel after, contributing to prevent vessel wall injuries and relevant calcification detachment, whilst preventing emboli release. In addition, the filter has a distal closure mechanism, to be used prior to retrieve the device preventing upstream emboli release at closure. Furthermore, protection of cerebral and peripheral circulation is guaranteed both for macroemboli and microemboli, thanks to adequate filter mesh pore selection.

Preferably, the device according to the invention comprises a transcatheter intraprocedural filter prosthesis for blood vessel (in particular aorta vessel) that includes a tubular filter, expandable distal and proximal support structures; said tubular filter forming a tubular shape when deployed, with a distal end being normally open and a proximal port normally closed. The complete collapsing and deployment of the filter is enabled by the relative linear movement of an external shaft with respect to an internal support catheter.

In a specific intra-aortic embodiment, the distal end of the deployed filter is positioned in ascending aorta, upstream respect to innominate artery, and the proximal end is positioned in descending aorta, downstream respect to the end of aortic arch.

In another specific embodiment, the funnel configuration can be modified during the procedure by maintaining its apex downstream or reverted inside the filter main body or in an intermediate position.

The device can be completely or partially collapsed during the procedure in order to be re-positioned. At the end of the procedure both the distal and proximal closure mechanisms are activated, then the device is collapsed, retracted inside the shaft and fully retrieved out from the patient.

The filter device is intended to be inserted prior to start other transcatheter procedures and to be retrieved after other transcatheter devices removal.

In summary, the filter device here described is adapted to guarantee an antiembolic protection ensuring navigation of other working catheters into the filter, permanent closure at the proximal end and closure at the distal end before filter retrieve, thus giving advantages respect to existing devices and methods.

DETAILED DESCRIPTION OF THE INVENTION

The invention will be better understood below, in association with some illustrated examples.

BRIEF DESCRIPTION OF THE FIGURES

FIG. 11*a* Ascending aorta with guide wire (29)

FIG. 11*b* Navigation of the collapsed filter device (1) along the aortic arch (25)

FIG. 11*c* Device deployment at the intended location

FIG. 11*d* Interaction between the device, pig tail and other working catheters (31)

FIG. 11*e* Emboli entrapment and Blood Flow direction through the device

FIG. 11*f* Proximal (14) and distal closure (15) activation

FIG. 11*g* Filter device retrieved after procedure

NUMERICAL REFERENCES USED IN THE FIGURES

Device Related Items

Figure 1:
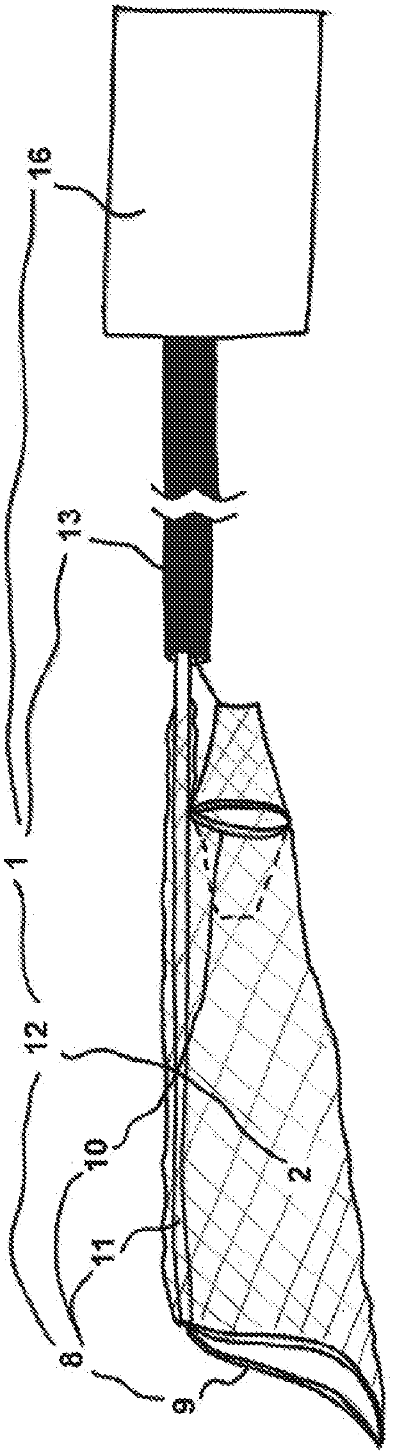
FIG. 1 Filter device assembly in the active configuration, including a filter-structure-catheter assembly (12), an external shaft (13), a handle (16)

1 transcatheter filter device
2 tubular filter
3 main body of the tubular filter
4 funnel
5 distal end of the tubular filter
6 proximal end of the tubular filter
7 port of the tubular filter (coincident with the funnel apex)
8 structure assembly
9 distal structure
  a. embodiment with one ring
  b. embodiment with two rings assembly
10 proximal structure
11 supporting catheter
12 filter-structure-catheter assembly
13 external shaft
14 proximal closure system
  a. self-sealing automatic closure mechanism (a-a; a-b: two different embodiments)
  b. mechanical closure mechanism (b1 open; b2 closed)
15 distal closure system
16 handle and relevant commands, which can comprise the following elements:
  a. command for external shaft (13) movement
  b. command for distal structure (9) trim
  c. command for funnel (4) movement
  d. command for proximal port (7) activation
  e. command for distal port (7) activation
  f. flushing port for guide wire (29)
  g. flushing port for external shaft (13)
17 tip
18 artificial valve
19 radiopaque markers Anatomy References

20 Aortic valve
21 Coronary ostia
22 Sinu Tubular Junction
23 Ascending aorta
24 Innominate artery
25 Aortic arch
26 Descending aorta
27 Femoral access Working Catheters and Other Accessories

28 Introducer
29 Guidewire
30 Pigtail
31 Working catheter
32 Funnel lower stitching line
33 Funnel upper stitching line
34 Intermediate structure (example A)
35 Intermediate structure (example B)

In one embodiment, the antiembolic filter device comprises the following macro elements (FIG. 1): an assembly 12, which includes a tubular filter 2 adapted to retain emboli, whilst allowing blood flow, a structure assembly 8 to sustain the filter and make it couple with a vessel, an external shaft 13 to collapse/track/deploy/retrieve said assembly and a handle 16 to enable with specific commands said operations, together with the optimal sealing with the vessel and the interaction with other devices.

Figure 1A:
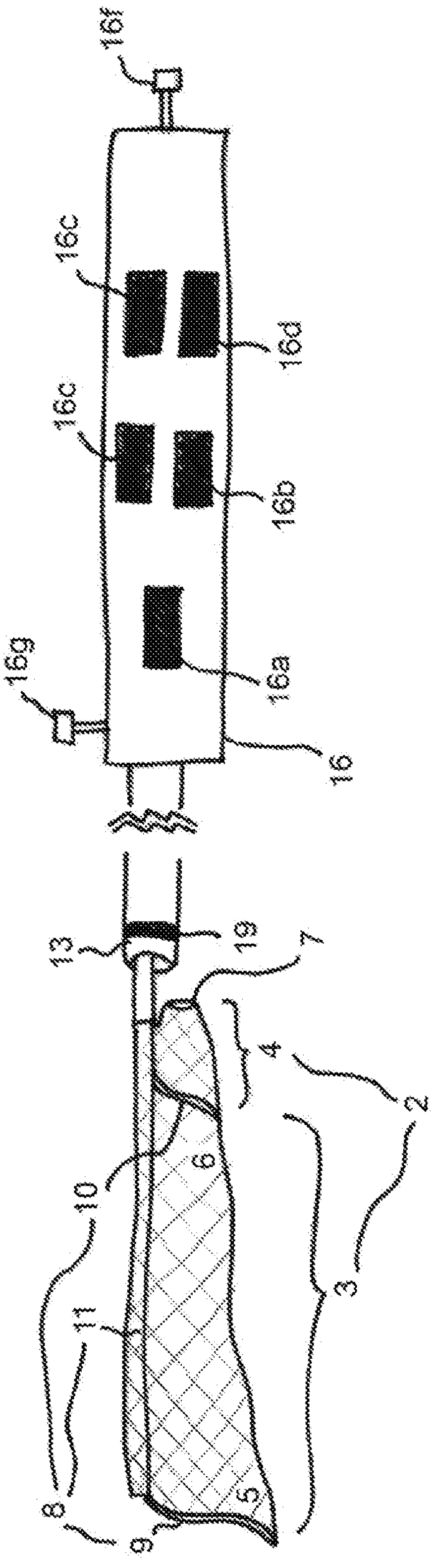
FIG. 1*a* Filter device components nomenclature
Figure 1B:
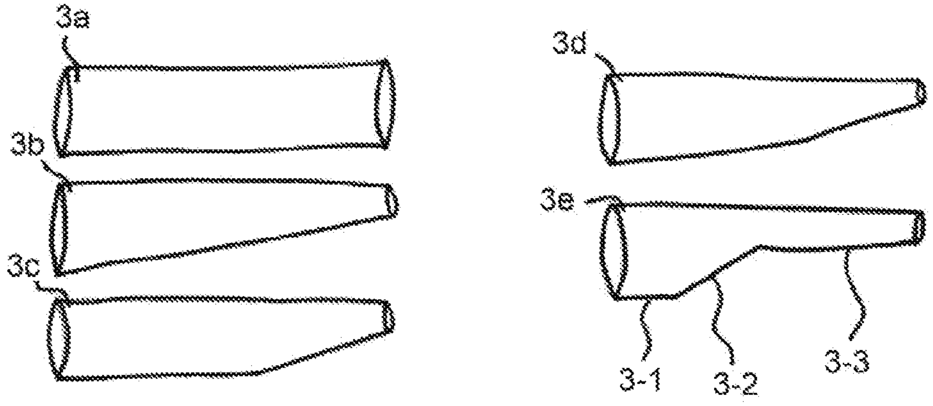
FIG. 1*b* Main body of the filter (3): some examples of geometries (a) cylindrical shape, b) conical shape, c) cylindro-conical shape, d) double conical shape, e) multi angle shape)
Figure 1C:
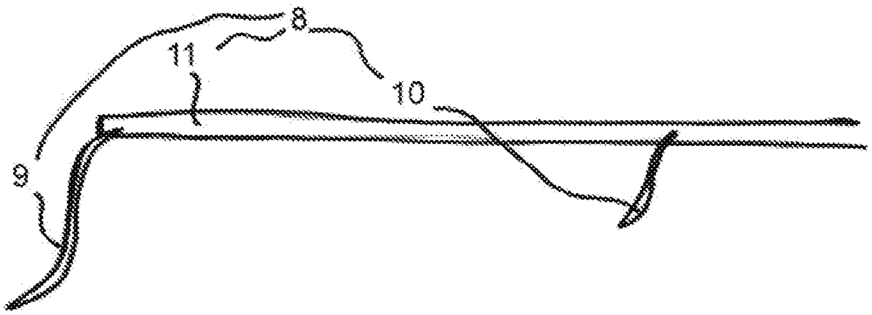
FIG. 1*c* Support structure assembly example (8)

The tubular filter 2 is placed externally to the structure assembly 8, as shown in FIG. 1: this assembly comprises a distal support structures 9, placed upstream respect to the blood flow direction and intended to make a leak-free coupling of the filter with the vessel, a proximal support structure 10, defining the region where the emboli are collected and where other devices pass inside the filter by crossing relevant port 7, and a supporting catheter 11, as shown in FIG. 1*c*. In specific embodiments, said tubular filter 2, structure assembly 8, external shaft 13 and handle 16 are permanently joined.

In specific embodiments (FIG. 2, 3), said filter device is adapted to be used as an intra-aortic protection, extending from the ascending aorta 23, upstream with respect to the innominate artery 24, to the descending aorta 26.

FIG. 1*a* show the main components of said filter device 1 here below described starting from the tubular filter 2 components, then going to the structure 8, shaft 13, handle 16.

The tubular filter 2 is preferably made of a low friction porous and flexible polymeric or composite material, here including polyester or polyamide, with mesh pore preferably lower than 150 microns. It can be coated with either a hydrophilic, low friction or anti-thrombogenic coating or a combination of thereof. Filter material, coating and shape facilitate the navigation of transcatheter devices into its body, both during the insertion and the retrieval, preventing relevant direct contact with the vessel wall, that can make injuries on it. Specific embodiments comprise perforated membranes and fabrics. In one embodiment a woven fabric can be chosen, with warp and weft either made by multi-filament or monofilament yarn, with an either constant or variable weaving pattern, thus resulting in a pore comprised amongst the square and the circular geometry and either constant or variable mesh pore and open area along the filter longitudinal and circumferential directions.

The tubular filter 2 is geometrically defined by a distal element and a proximal element, namely a main body 3 and a funnel 4 (FIG. 1*a*). The main body 3 comprises a distal end 5 and a proximal end 6; said distal end 5 is adapted to be open when the device is in active configuration, hermetically coupled with the vessel and closed before the device retraction; said proximal end 6 that is adapted to be open in the active configuration; said funnel 4 forming an extension of said main body 3, with the funnel base located at said proximal end (6).

Embodiments for the filter main body 3 (FIG. 1*b*) include a cylindrical body, a conical body and combination thereof. Specific embodiments for intra-aortic procedures comprise a three regions main body 3*e* (FIG. 1*b*), with a distal cylindrical part coupling with the aorta 3-1, an intermediate conical part 3-2 having a progressively decreasing diameter and a proximal cylindrical part 3-3, with: said intermediate part shaped to reduce relevant pressure drop for blood circulation and the overall filter encumbrance along the internal side of the aortic arch 25; said proximal cylindrical part geometry intended to allow free forward and back movement of working catheters, even in case of retrieve of partially re-collapsed TAVIs in descending aorta. The length of the main body is generally comprised from 10 to 30 cm, in order to be adapted to extend for all the vessel length to be protected from the ascending aorta 23, upstream with respect to the innominate artery 24, to the descending aorta 26.

Embodiments for the funnel 4 include movable and fixed funnels, with either symmetric or asymmetric shapes.

Figure 4:
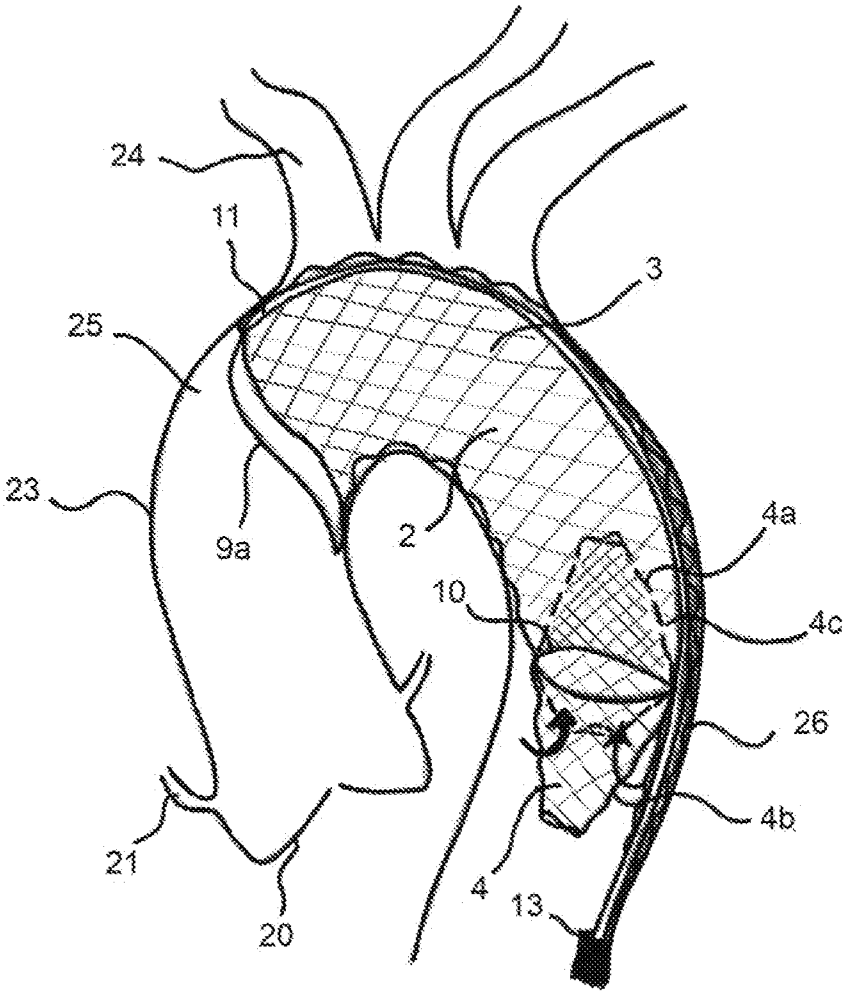
FIG. 4*a* Movable funnel in the not active configuration (funnel downstream)
FIG. 4*b* Movable funnel in the active configuration (funnel reverted inside main body)
Figure 4A:
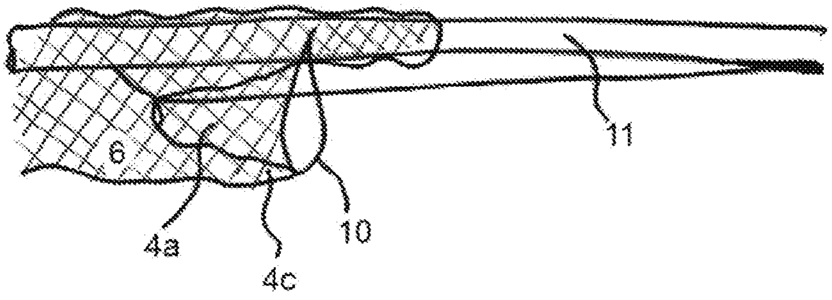
Figure 4B:
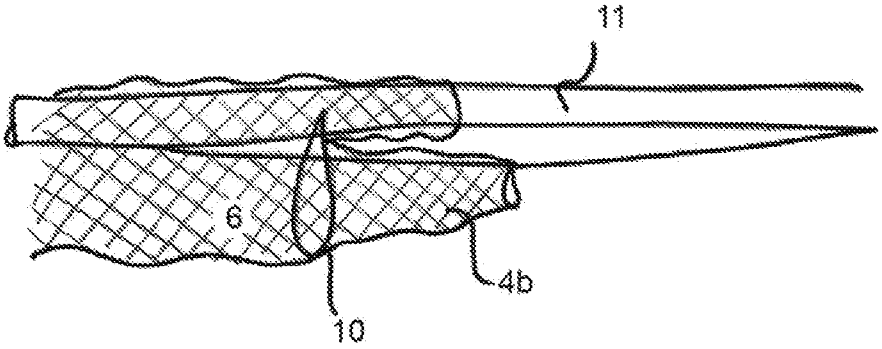

FIG. 4 shows an embodiment of a movable funnel 4, with funnel in its extreme configurations: a first position (detailed in FIG. 4*b*), in which the funnel apex is proximal with respect to main body 3 proximal open end 6 and a second position (detailed in FIG. 4*a*), in which the funnel apex is positioned within said main body, between said main body 3 distal and proximal ends. In the active configuration, the funnel top is generally positioned inside the main body, thus acting as a sliding conveyor for working catheters that cross it, whilst gathering the emboli in the interspace amongst the main body and the funnel 4*c*, this making the interaction between the working catheter and the funnel port intrinsically free from emboli. In this embodiment, the funnel is oriented by acting on the apex, i.e. with a push-pull system commanded by the handle as detailed in FIGS. 4*b* and 4*a*, this embodiment allowing to move the funnel also whilst a working catheter crosses it.

Figure 5:
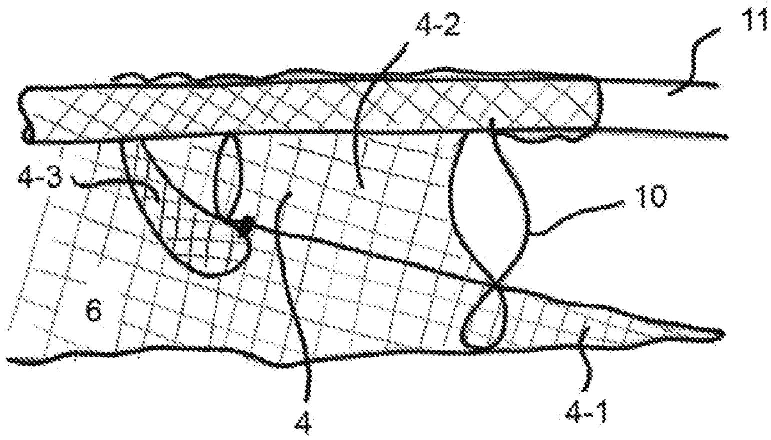
FIG. 5 Fixed funnel embodiment (4) example, with a "8" shaped proximal structure (10)

A second embodiment for the funnel (FIG. 5) comprises a fixed funnel element with distal apex 4-2, enabling the crossing of working catheters, joined to the following elements: laterally, to a fixed conical element, being the proximal part of the main body 3, with proximal apex 4-1 adapted to collect emboli; to a proximal ring 10, shaped as a "8", that defines the base of the funnel and of the collecting conical element; to a flap 4-3, with distal end base either connected to the filter main body 3 or to the supporting catheter 11 and proximal end connected at least in a single point to the funnel 4-2, this flap adapted to prevent emboli release downstream, whilst allowing the funnel to be crossed.

Figure 6:
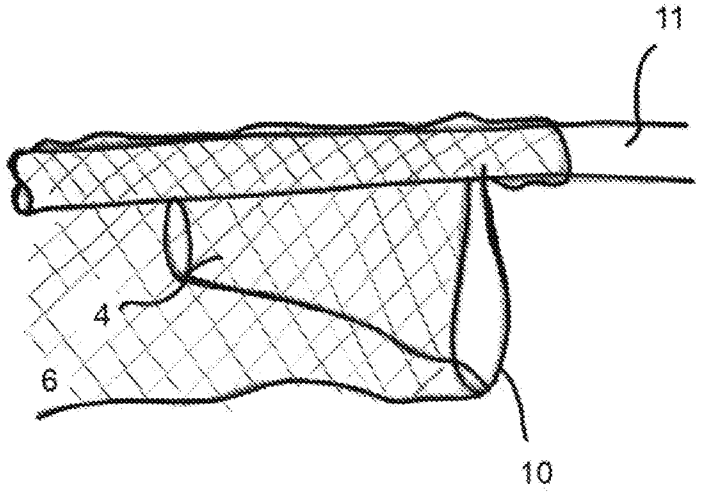
FIG. 6 Fixed funnel embodiment (4), with a ring shaped proximal structure (10)

In a third embodiment for the funnel (FIG. 6), it comprises an orientation fixed funnel element with the base open at the proximal end in the active configuration, acting as a conveyor; this funnel being joined to at least the following elements: laterally, to a fixed conical element, being the proximal part of the main body 3, with the apex closed at the proximal end; to a radially expandable proximal structure (10), said proximal structure either being manually activated or self-expandable.

The funnel element is generally positioned in a straight portion of the vessel, in order to ensure easy crossing of working catheters at its apex. The funnel is shorter than main body, with a ratio of the funnel to main body length is generally comprised between 1/10 and 1/3, depending on the specific vessel centerline length, shape and vessel diameter. Specific intra-aortic embodiments have a funnel length generally comprised between 2 and 10 cm.

Figure 7A:
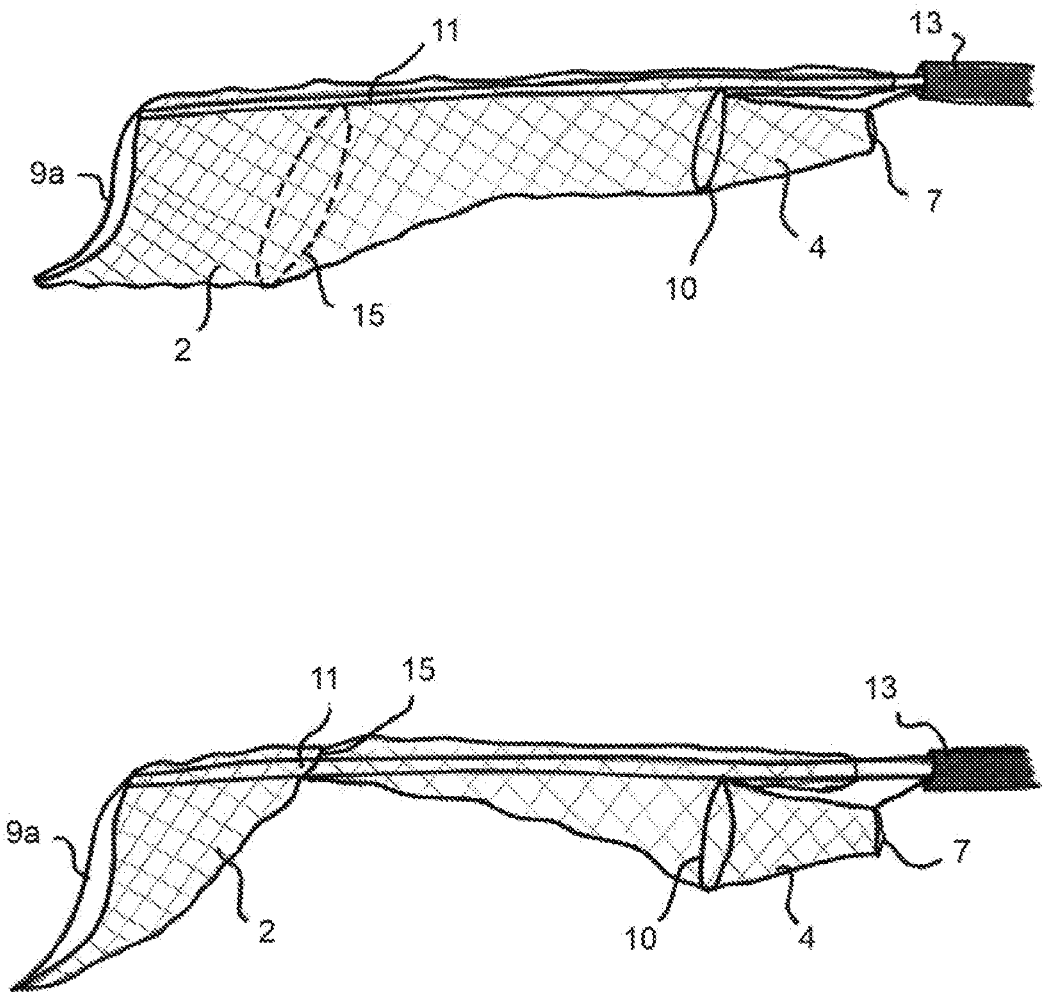
FIG. 7*a* Distal closure mechanism (15) example
Figure 7B:
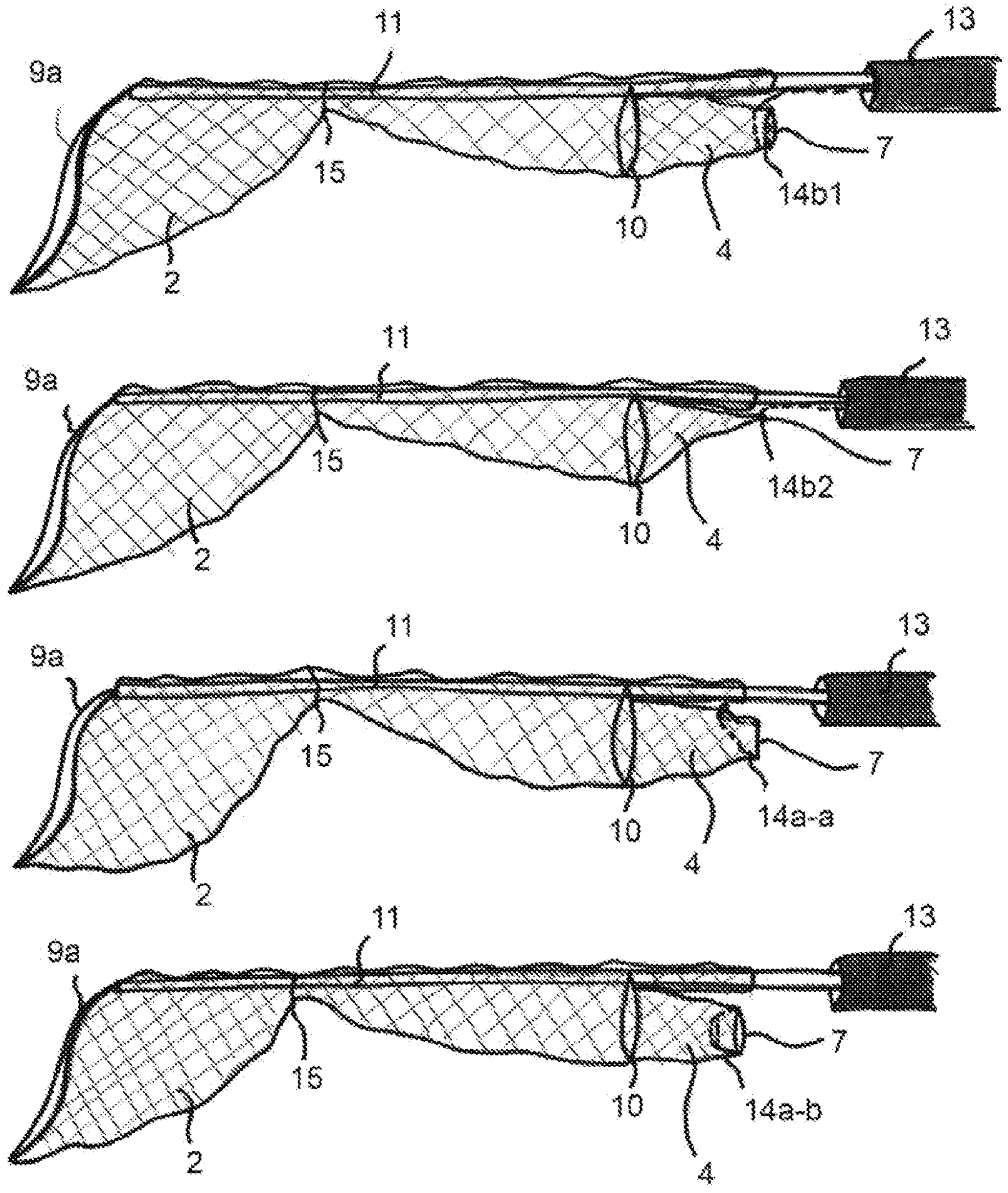
FIG. 7*b* Proximal closure mechanism (14) example

The proximal closure system 14 preventing downstream emboli release, which is positioned at the funnel 4 apex is referred as the filter proximal port 7: it can either consists of a funnel geometry shaped in order to have the apex oriented downstream respect to the blood flow or consists of a folded top or a combination of thereof systems or consists of an actual closure system; an example of closure system is constructed by a lazoo system activated by a wire, either manually 14*b* or automatically 14*a*, thanks to an elastic wire. FIG. 7*b* shows examples of proximal port applied to a movable funnel systems: in the two pictures at the top, a mechanical closure mechanism is shown in the open b1 and closed b2 positions, whilst in the two pictures at the bottom two different self-sealing automatic closure embodiments are shown a-a; a-b.

The distal closure system 15, used to prevent upstream dislodgement at the end of the procedure, is activated before recollapsing the device (FIG. 7*a*), being either a lazoo system, manually activated, or an automatic elastic system, which is manually deactivated in the active configuration.

A specific embodiment of the support structure assembly 8 is shown in FIG. 1*c*; it comprises at least: a supporting catheter 11 extending within the main body, one radially expandable distal structure 9 joined to said main body distal end, one radially expandable proximal structure 10 positioned at said main body proximal end level, said distal structure 9 and said proximal structure 10 being fixed to said supporting catheter 11.

Figure 2:
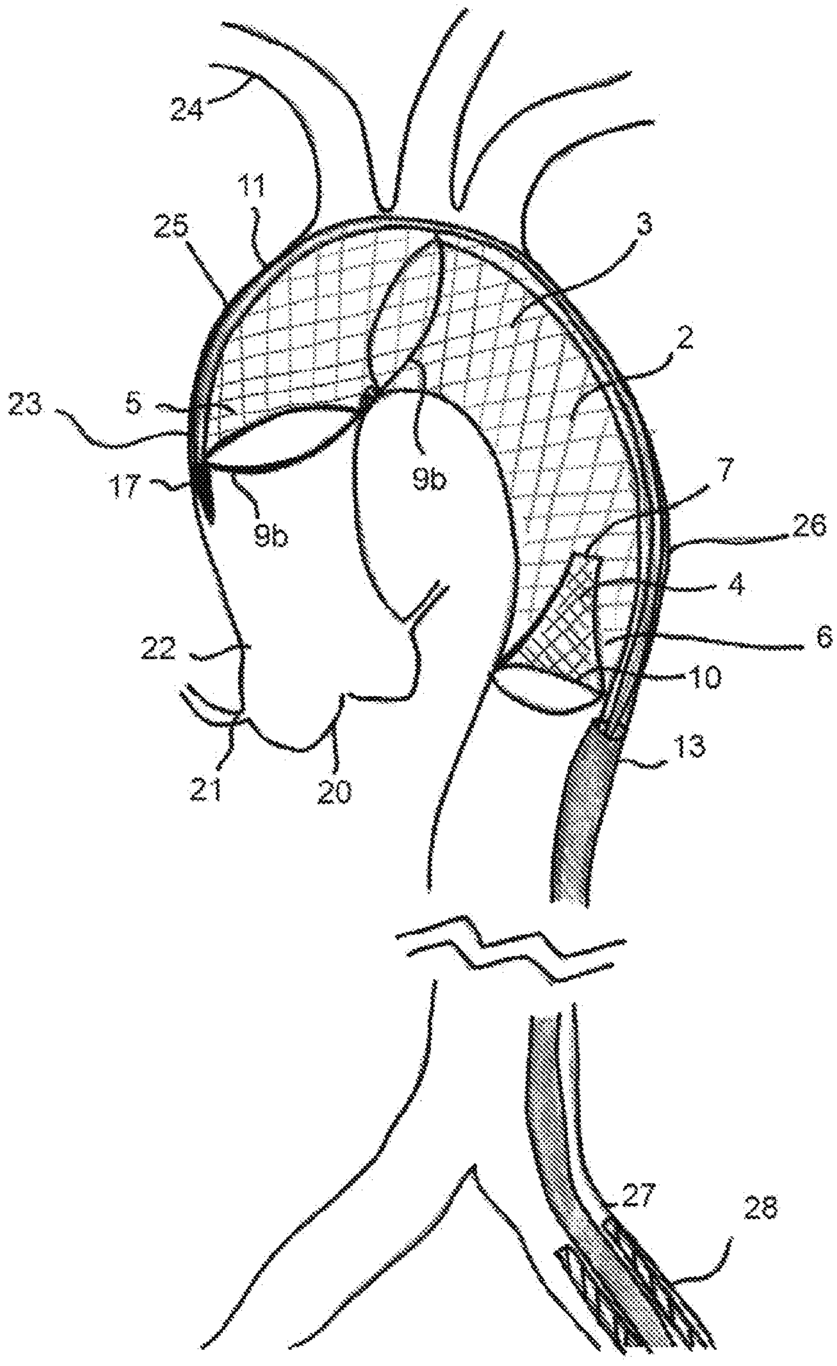
FIG. 2 Two distal rings structure embodiment (9*b*) example in the active configuration FIG. 2*a* Adaptative mechanism of the two distal rings structure embodiment FIG. 2*b* Retraction mechanism of the two distal rings structure embodiment FIG. 3 One distal ring structure embodiment (9*a*) example in the active configuration FIG. 3*a* Adaptative mechanism of the one distal ring structure embodiment FIG. 3*b* Retraction mechanism of the one distal ring structure embodiment FIG. 4 Movable proximal funnel embodiment (4)
Figure 3:
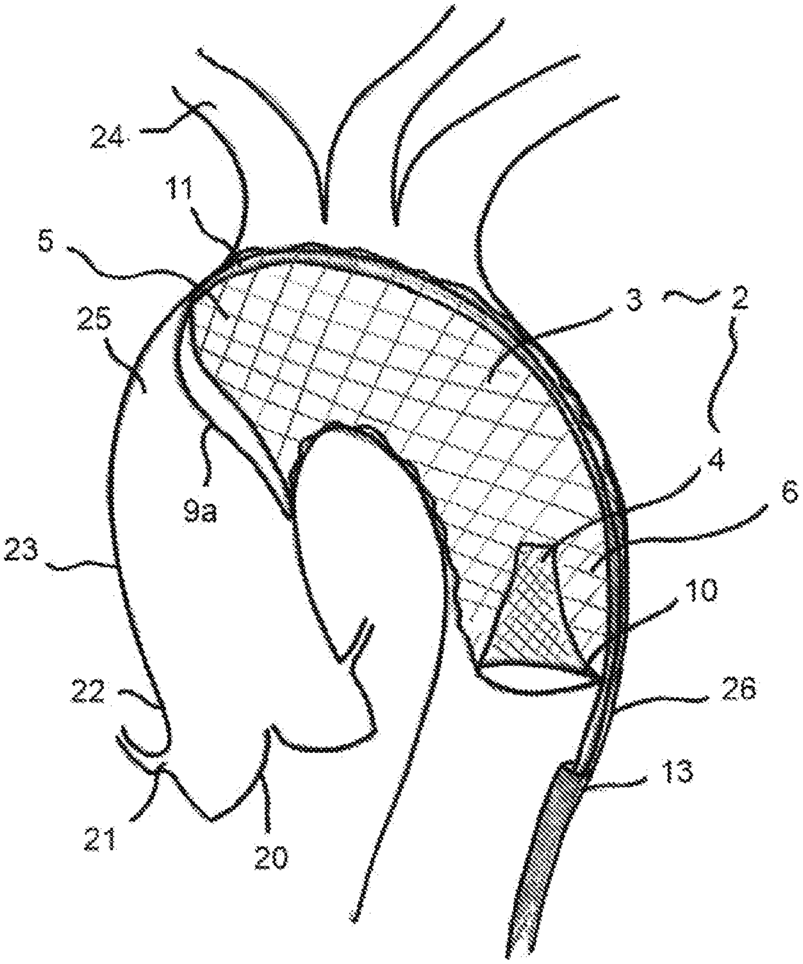

FIG. 2 and FIG. 3 show two intra-aortic embodiments of the filter device 1 in the active configuration, differing on the distal structure 9 element. In both cases, the mechanical stability of the filter device, either in a standalone condition or when crossed by other working catheters, is ensured at least by the coupling of the distal structure 9 with the ascending aorta vessel and by the coupling of the supporting catheter 11 with the aortic arch.

The radial expandable characteristics of the distal structure ensure to cover a broad range of geometry (with ascending aorta diameter usually ranging between 20 and 40 mm) and anatomies with a reduced number of sizes for the filter device without risk of device dislodgment or migration.

In the specific embodiment shown in FIG. 2, the distal 9 structure comprises two rings elements 9*b*, here referred as the more proximal and the more distal elements, mutually joined: the more distal ring element is joined to the catheter 11 at its distal end, to the more proximal ring element at its proximal end and to the distal end of the main body 3 along its perimeter; the more proximal element is connected at its proximal end to a specific handle sealing command by a rod, passing inside a lumen of the supporting catheter 11. This structure can be either constructed of a single wire or multiple wires having either a circular, elliptical or rectangular section, or a combination thereof; the joinings amongst the components can be made by crimping, welding, gluing, binding or, in case of wire elements by twisting them, or with a combination of thereof methods.

Figure 2A:
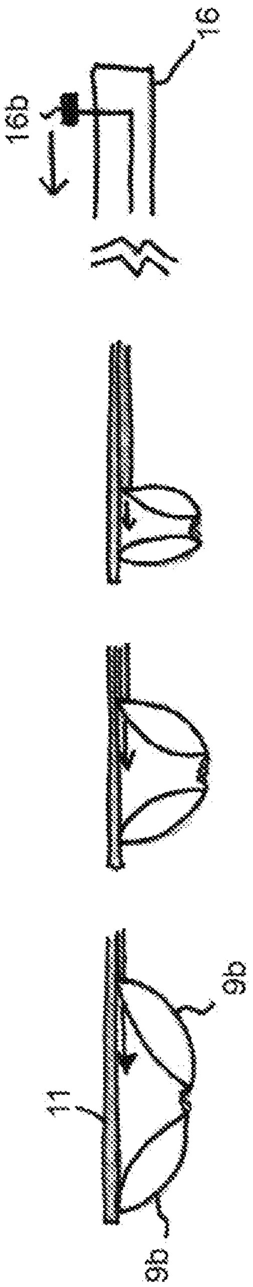
Figure 2B:
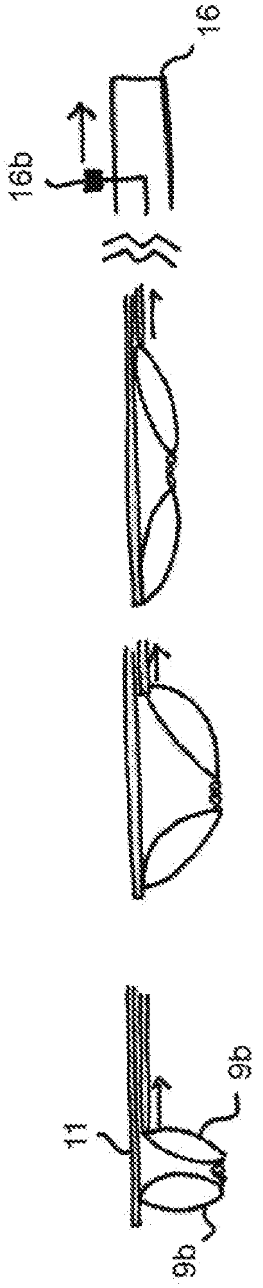
Figure 9:
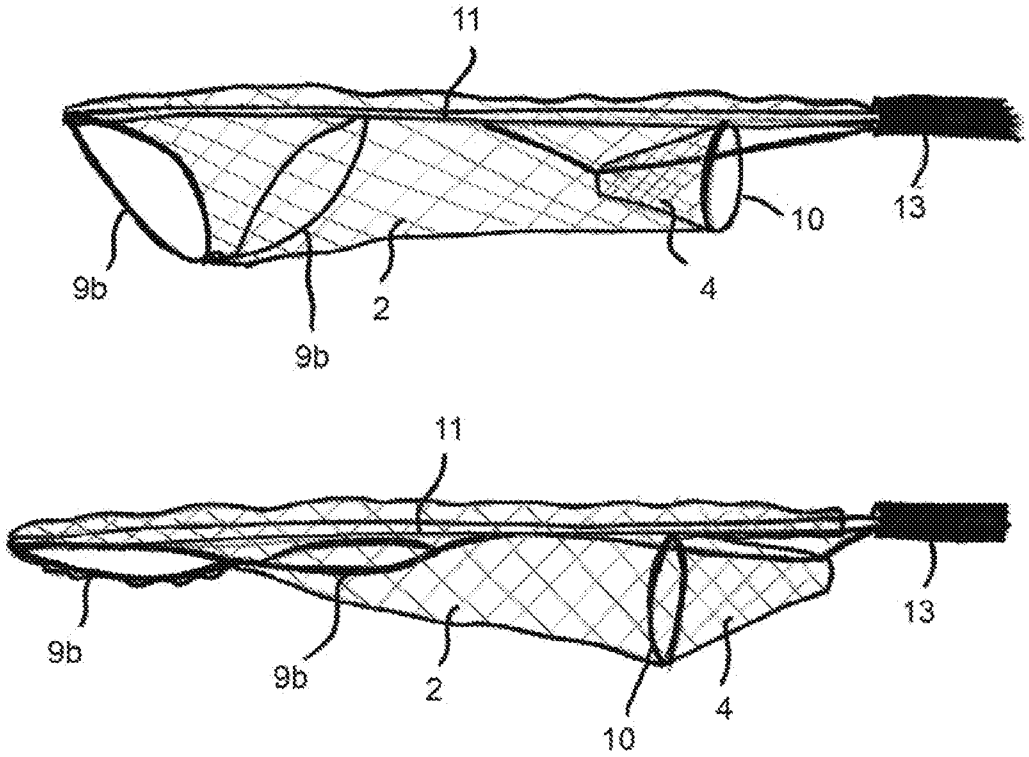
FIG. 9 Integration of the movement mechanisms for distal structure (9*b*) and funnel (4)

The distal ring element is designed to radially expand conforming to the aorta in the active configuration, thus guaranteeing a leak-free coupling: this is ensured by the high elasticity limit of the material used, preferably but not exclusively being Nitinol, by its geometry, with perimeter larger than the aorta vessel, by relevant axis free orientation, tilted respect to aorta centerline and by relevant deformation mechanisms commanded by the handle. As an example, by actively pushing on the sealing handle command (forward movement on the command 16*b*: FIG. 2*a*), the proximal ring element pushes onto the distal one, thus partially tilting relevant ring plane and resulting in radial compression onto the aortic wall. In this embodiment the pulling handle command (backward movement on the command 16*b*: FIG. 2*b*) can be adopted in order to close the filter main body distal end without using specific commands. In a further specific configuration, which is shown in FIG. 9, the interconnection amongst distal ring and funnel commands can act simultaneously on the closure mechanism of the filter distal end and on the movement of the funnel apex, thus simplifying the handle mechanism and the operations to be carried out prior to the device retrieve.

Figure 3A:
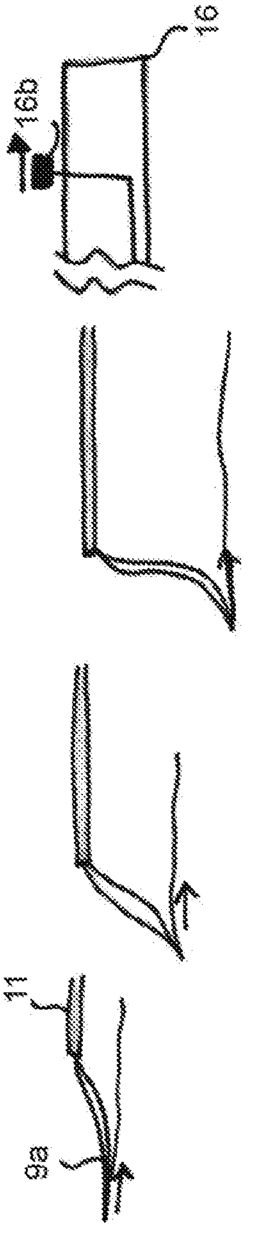
Figure 3B:
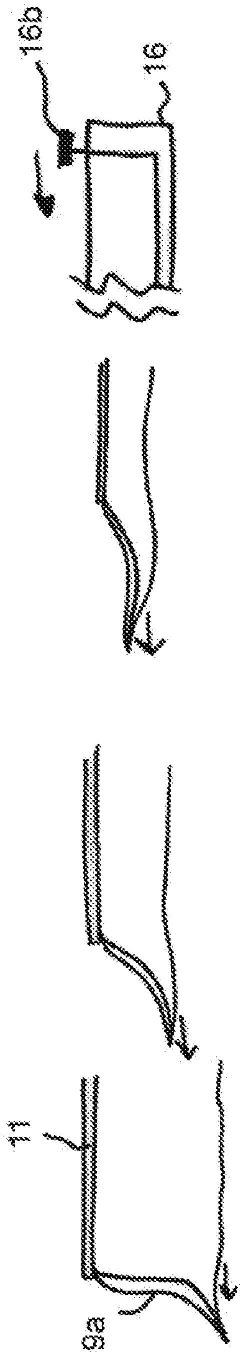

In the embodiment shown in FIG. 3, the distal 9 structure comprises one ring element 9*a*, with proximal end joined to the catheter 11, perimeter joined at the distal end of the main body 3, distal end joined to a single or multiple wire passing inside the filter and connected to a specific handle sealing command. In this case the radial expansion of the ring (FIG. 3*a*), for which apply considerations similar to the distal ring element referred in FIG. 2*a*, is ensured by a pulling system rather than a pushing system command.

A specific embodiment of the proximal structure 10 is shown in FIG. 4, with structure shaped as a ring and connected to the supporting catheter. The ring defines the base of the funnel 4, allowing to orient it either in the proximal and distal directions, by tilting its apex by specific commands connected to the handle. In the embodiment shown, the ring doesn't couple with the descending aorta. In other embodiments the proximal structure 10 can be shaped similarly respect to the distal structure 9, thus allowing to radially couple with the aorta vessel.

Specific embodiments can be constructed wherein structures intermediate respect to the distal 9 and proximal 10 can be connected to the supporting catheter 11, in order to increase the device stability and contribute to fully expand the tubular filter main body.

Figure 8:
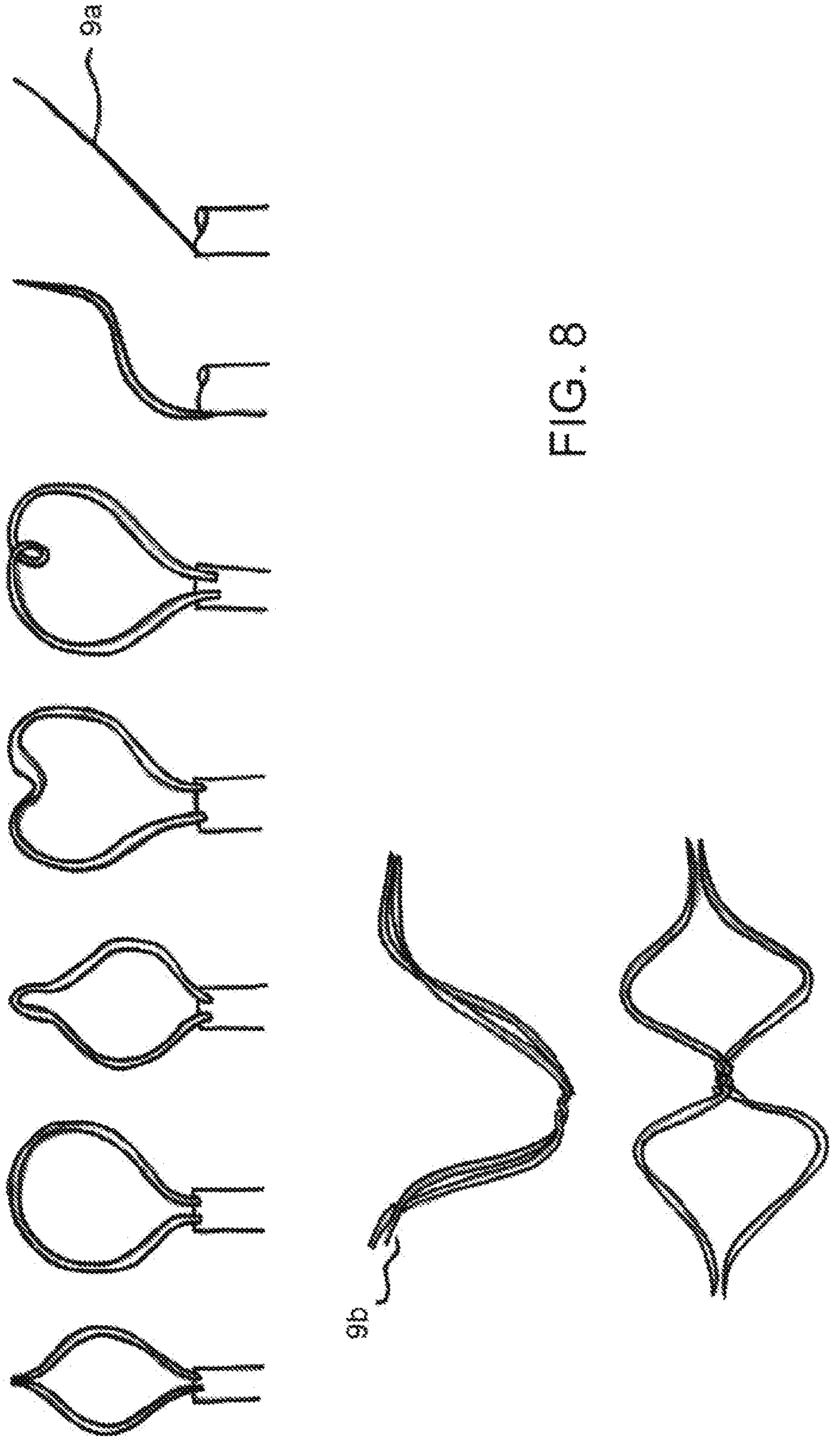
FIG. 8 Rings configuration examples

For both the distal and proximal, and where applicable intermediate, structures, the overall geometry can be elliptical in plan view, but also differently shaped as shown in FIG. 8; similarly, lateral view can show a planar structure but also a "S" shaped lateral profile to enhance leak-free conforming to the aortic arch, as shown in FIG. 8.

The supporting catheter 11, which is joined to the distal 9 and proximal 10 structures and to the tubular filter 2, adapts in the active configuration at the extrados of the aortic arch and sustains all the loads arising from the procedure (see FIG. 11): at this purpose it can be made by a flexible polymeric or a composite material, here including a metal braided polymer, selected as the best compromise amongst high elongation/compression/torsion stiffness and fairly high flexibility. The supporting catheter 11 profile is adapted to house inside specific lumens, the commands to crimp/deploy the filter 2, to act on the distal 9 and proximal 10 structures and on the distal and proximal filter closure system, where applicable, and to house other accessories/working catheters, here including guide-wire, pig-tail and balloon catheters, here contributing to simplify the overall procedure.

Figure 10:
FIG. 10 Trackability and Navigation tools example: external shaft (13), radiopaque marker (19) and tip (17)

The external shaft 13, see details in FIGS. 10 and 11, is adapted to guide the collapsed filter assembly 12 in position and to allow the deployment/recapture of the device, by sliding backward and forward respect to the multilumen catheter. The external shaft 13 is made of a flexible polymeric or composite material and preferably a metal braided polymer, i.e with reduced tensile and compression elongation and with adequate flexural compliance to ensure optimal pushability when tracking the filter device along the aortic arch, thus allowing to adapt to the extrados curvature of aorta without forcing onto it and minimizing snacking whilst interacting with the supporting catheter to crimp/deploy the filter.

A tip 17 can be included in any of the said structures 9, 11 or external shaft 13 or other structures to allow adequate priming, easy crossing of the introducer and smooth navigation into the aorta (FIG. 2 and FIG. 10).

Figure 11A:
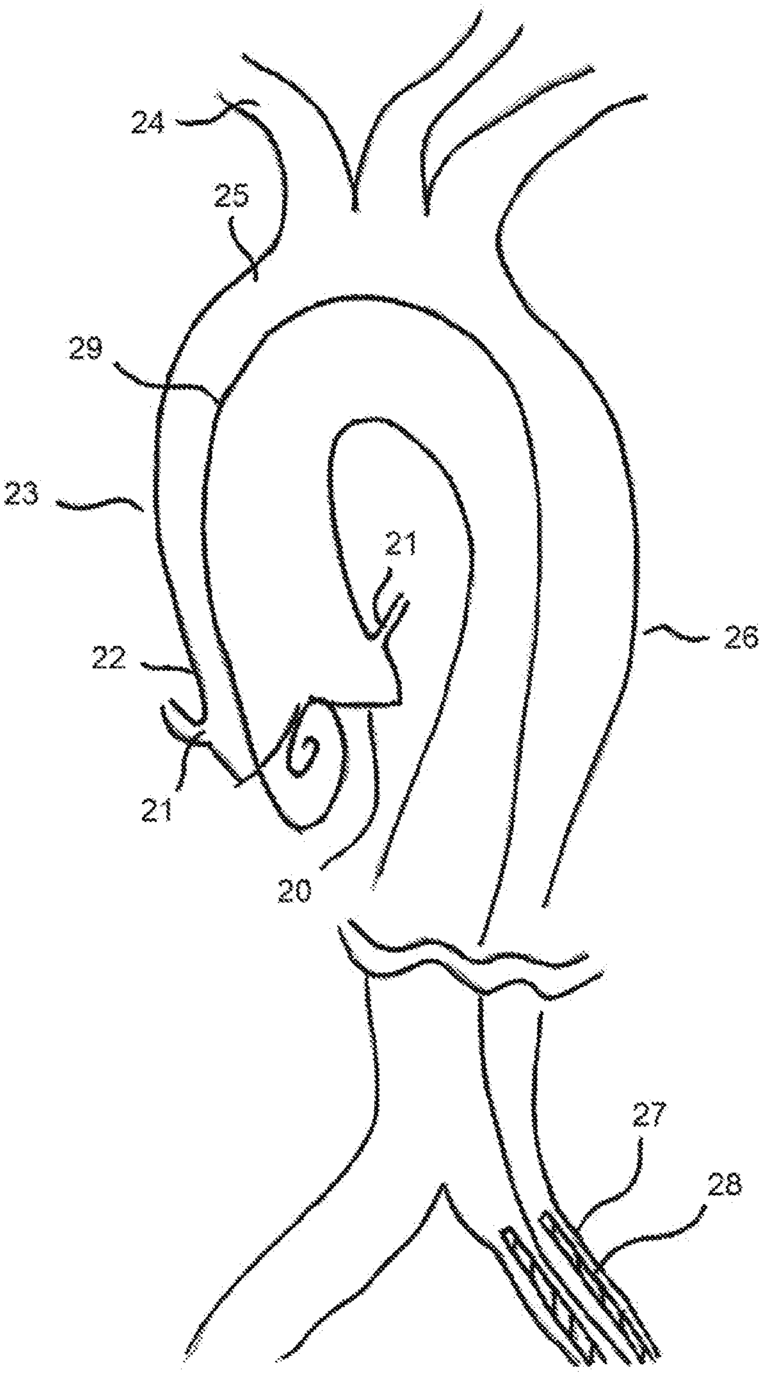
FIG. 11*a-g* Method for embolic protection: an intra-aortic procedure example
Figure 11B:
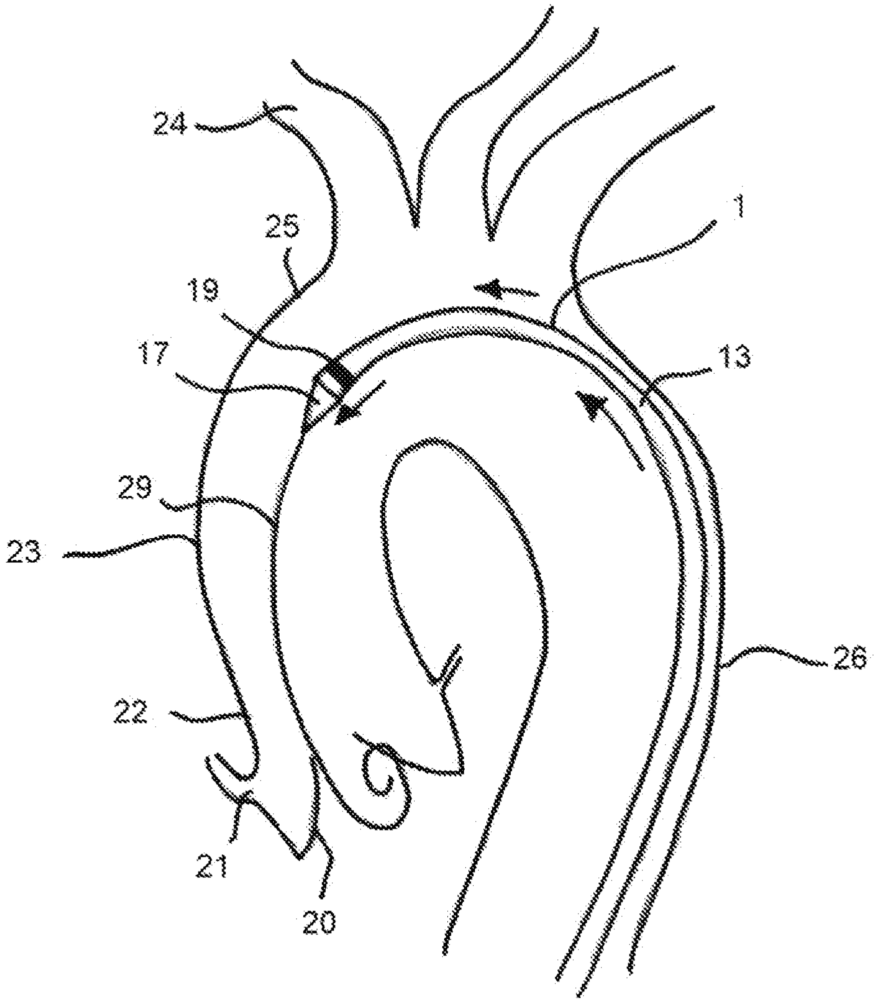

Radiopaque markers 19, see details in FIG. 10, FIG. 11*b*, can be joined to specific locations 11, 13, 9, 10 or other structures) in order to facilitate, via adequate imaging, the positioning of the device (1) and of other working catheters intended to cross it.

The handle 16 (FIG. 1*a*) allows specific commands including, where applicable, the sliding between an external shaft 13 and the supporting catheter 11, thus allowing filter crimping or deployment 16*a*, the activation of the distal closure mechanism 16*e*, the activation of proximal 14: 16*d* and distal 15: 16*e* closure mechanisms, the tensioning of the distal support structure 9: 16*b*, the funnel movement 16*c*, the flushing of the ports for guide wire 16*f* and external shaft 16*g*, the direct loading of other devices or accessories, not limited to a guide wire and/or a pig tail catheter and the enabling/disabling of an artificial valve 18, where applicable. The handle structure is made preferably but not exclusively by polymeric material; it houses all the commands, either made by rods or wires, and the proximal terminations of the supporting catheters 11 and of the external shaft 13, either directly or with the interposition of metal tubes. The handle can adopt either linear/rotatory mechanism to allow said movements and block systems, where applicable, to fix it in a determined position.

Here below a transcatheter procedure adopting the antiembolic filter device 1 is detailed, with specific features referring to an intra-aortic procedure, here comprising a TAVI, which allow cerebral and systemic emboli protection.

Figure 11C:
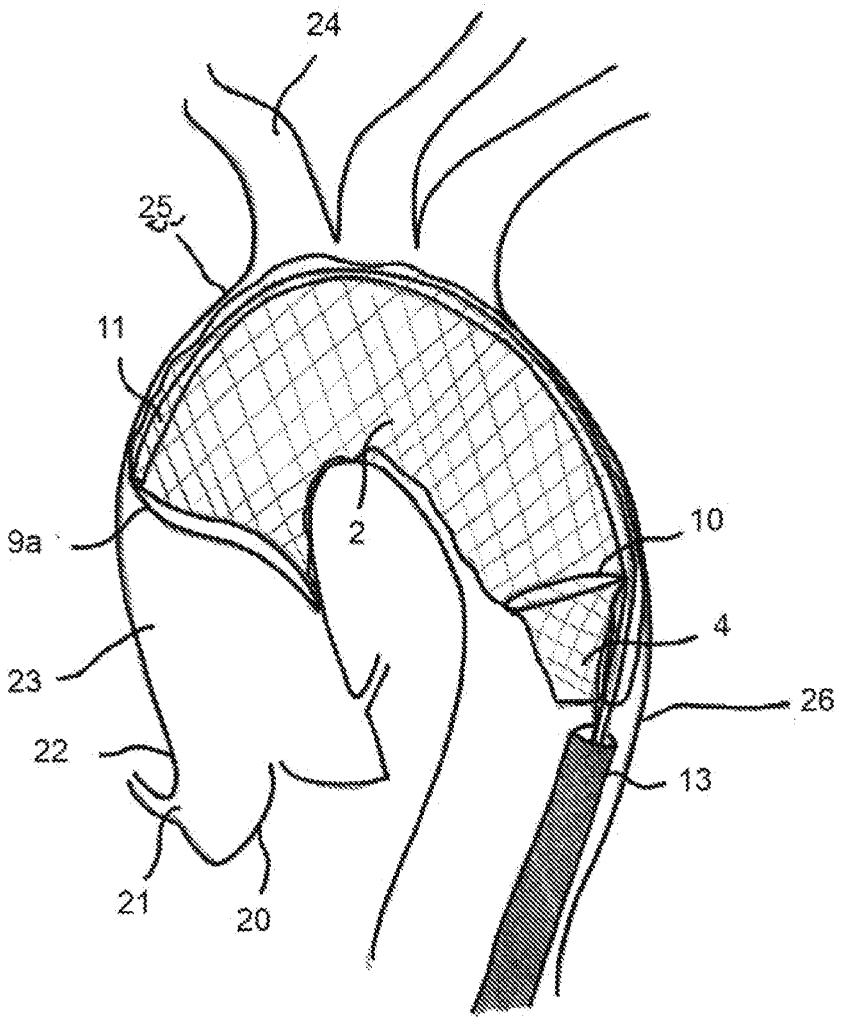
Figure 11D:
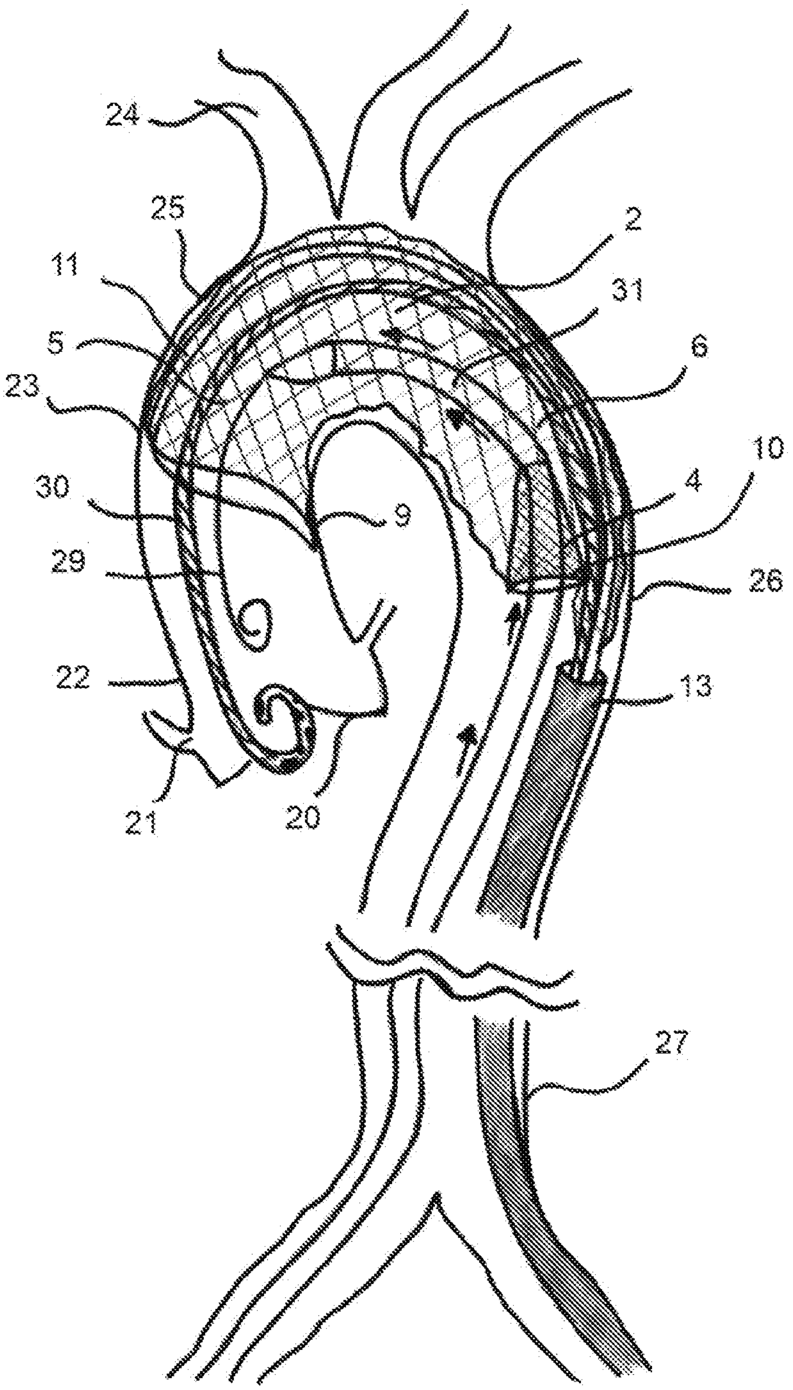
Figure 11E:
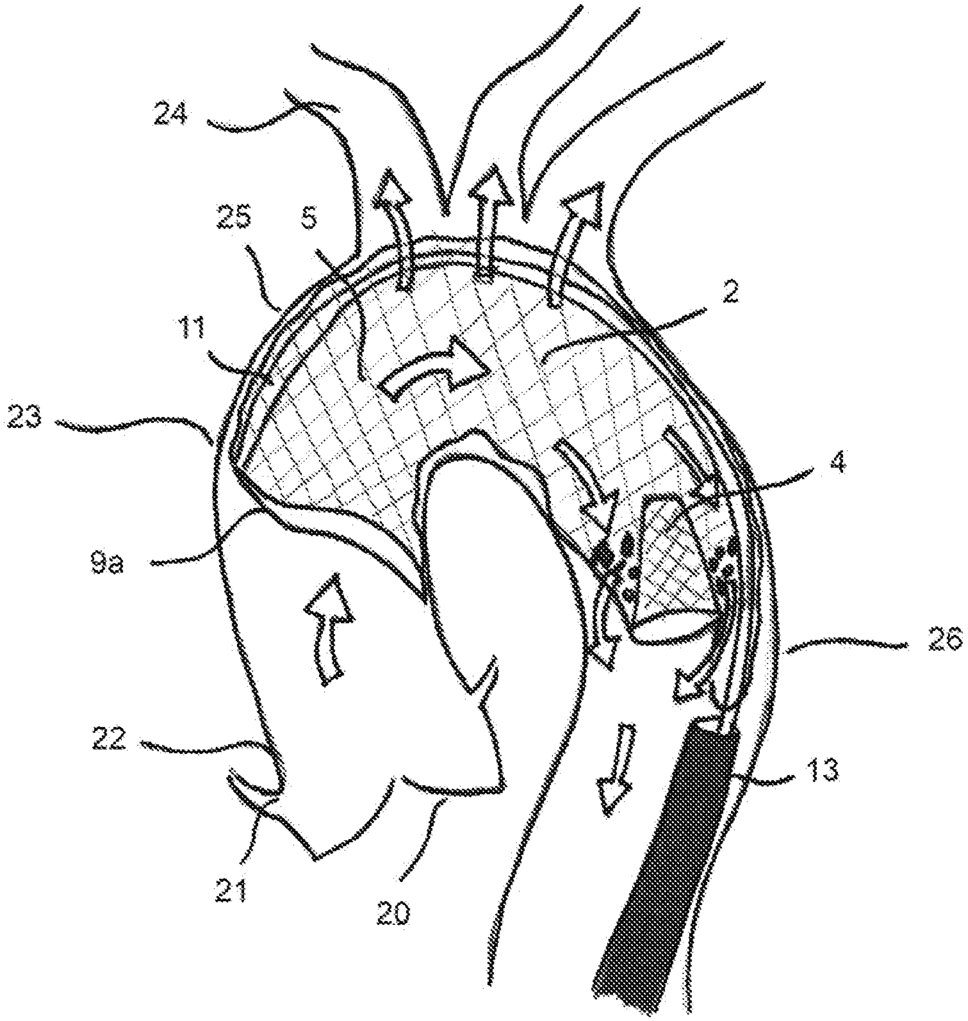
Figure 11F:
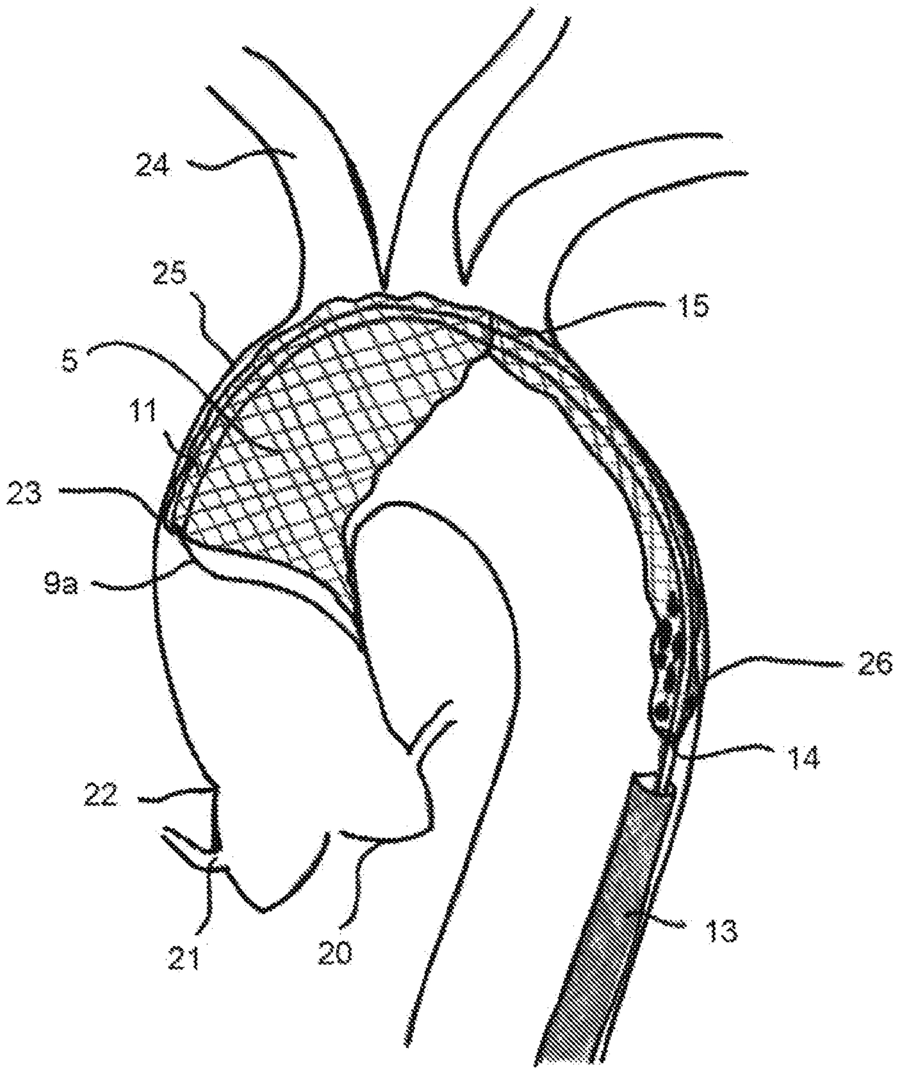
Figure 11G:
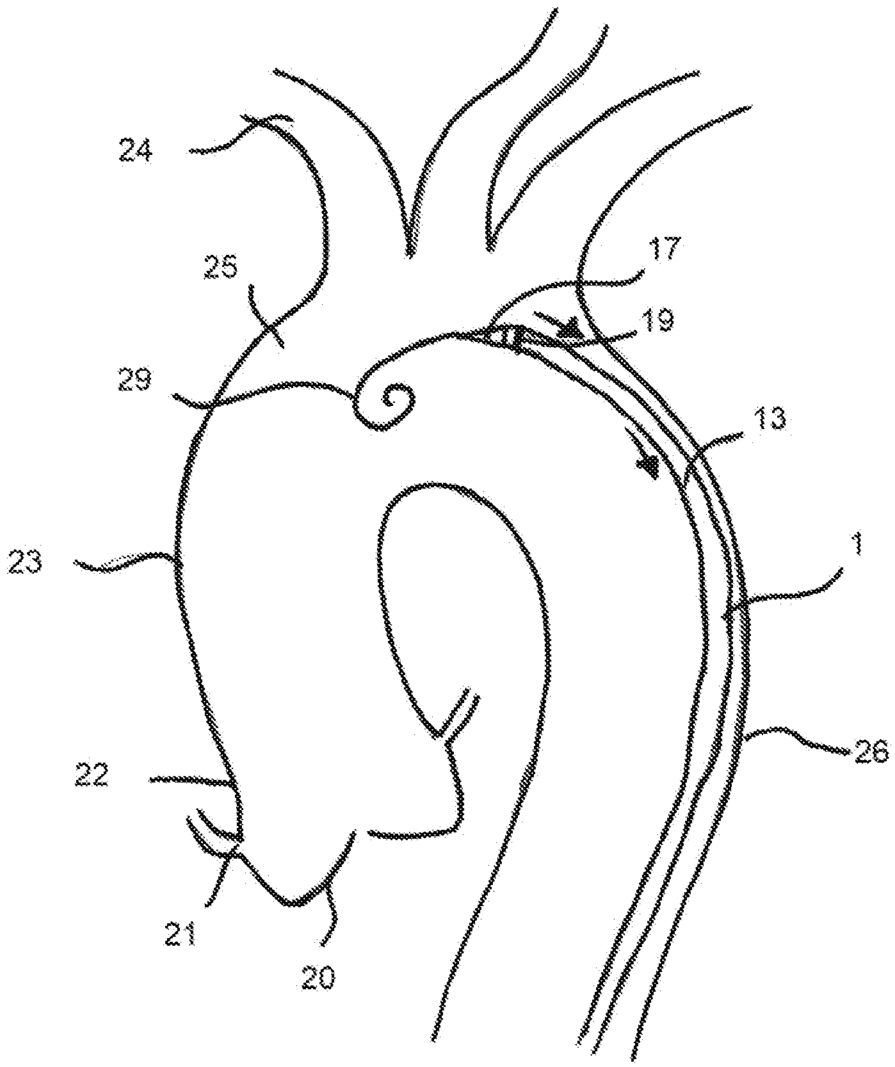

In this example, the antiembolic filter device 1 access is made from the femoral artery opposite (secondary) to that one (main) accessed by the working catheter 31 used for the prosthesis or the device to treat the aortic valve (FIG. 11*d*). Here below relevant procedure details:

a) An introducer 28 is inserted inside a femoral access 27.
b) A guide wire 29 is inserted inside the introducer 28 and navigated up to the aortic arch (FIG. 11*a*). As an option a pigtail is inserted and navigated up to the ascending aorta to allow a fluoroscopic imaging reference prior to the filter device insertion.
c) The filter device is collapsed, primed and debubbled into the external shaft catheter 13 before to introduce it into the arterial vessel (FIG. 11*b*).

d) The device is tracked along the vessel and positioned, with the aid of radiopaque markers and adequate imaging technique, the upstream respect to the innominate artery 24; the device is deployed and coupled with ascending aorta, by retracting the external shaft catheter 13 (FIG. 11*c*).

e) When the device is deployed, the distal end of the Filter 5 is fitting the aortic wall in order to convey all blood and possible debris into its funnel (FIG. 11*e*) thanks to the support structure 9, which circumferentially push the distal filter surface 5 against the aortic wall.

f) It is now possible to introduce the other working catheters inside the filter by crossing the funnel 4, whilst the funnel 4 and port 7 configuration prevents forward debris dislodgment. FIG. 11*d* shows the interaction amongst filter device and other working catheters normally used in a TAVI procedure.

g) At the end of the procedure the distal end of the filter 5, which in the expanded configuration remains open, can be closed, before the device recollapsing, in order to prevent any upstream debris dislodgment of the emboli collected at the proximal end of the device (FIG. 11*f*).

h) The device is completely re-collapsed by pushing distally the external shaft catheter 13, as shown in FIG. 11*g*. In this way, the device structures gradually collapse until reaching the distal end of the device safely keeping inside it all captured clots or calcium debris.

i) Finally, the overall device is retrieved.

Specific procedures can require partial closure, repositioning and re-deployment at different levels (e.g. from sinotubular junction to descending aorta) and, eventually, different supporting catheter positioning.

Moreover, procedures different respect to intra-aortic ones can require different geometrical arrangements of the abovementioned concepts, therefore this filter device can be applied in principle in any arterial or venous system requiring an antiembolic protection.

This method allows to deploy the filter device prior to the other working catheters 31, see FIG. 11*d*, and retrieve it after all the other working catheters, thus enabling to:

a) collect and retain emboli released during transcatheter procedures, with working devices eventually moving along the filter;

b) track working catheters inside the filter without direct contact to the vessel wall;

c) have the proximal port 14 of the filter generally closed during the whole procedure and the distal port 15 closed before the filter device is recollapsed and retrieved, thus preventing any downstream and upstream emboli release (FIG. 11*f*).

Figure 12A:
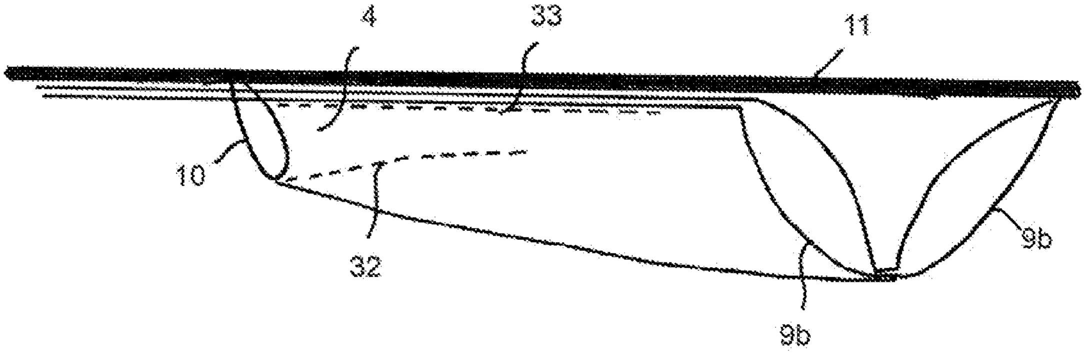
FIG. 12*a-d* Different filter examples with a funnel configuration defined by one or more stitching lines
Figure 12B:
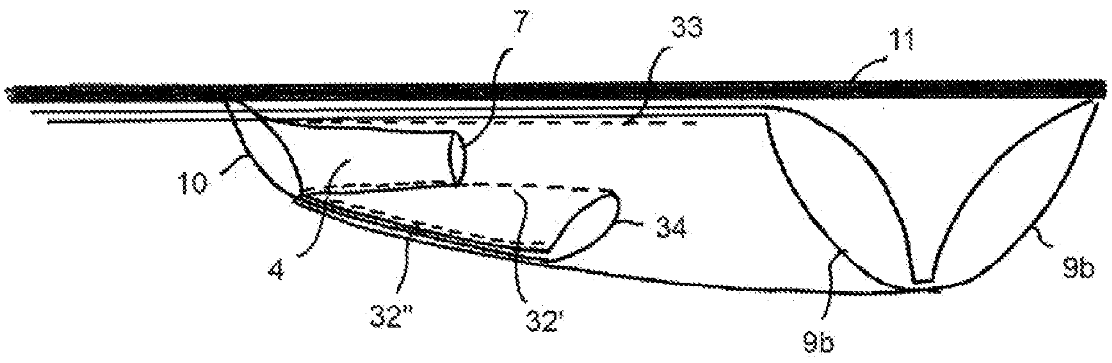

FIGS. 12*a* to 12*d* show different configurations of the funnel 4 and of a dead end to capture emboli generated during a procedure. The delimitation of the funnel 4 in FIG. 12*a* is obtained with two stitching lines 32,33 joining the two walls of the tubular filter 2. In particular the upper stitching line 33 is running all along the catheter body 11. The space between the upper stitching line 33 and the support 11 is dedicated to the distal structure 9*b*.

In another embodiment (FIG. 12*b*) the funnel 4 is delimited as in the embodiment of FIG. 12*a* while but tubular filter 2 furthermore contains an intermediate structure 34 for capturing emboli. The intermediate structure 34 has a conical shape defined between two stitching lines 32',32". The basis of the conical shape is located on the distal side and forms an emboli inflow mouth made by a rigid ring.

Figure 12C:
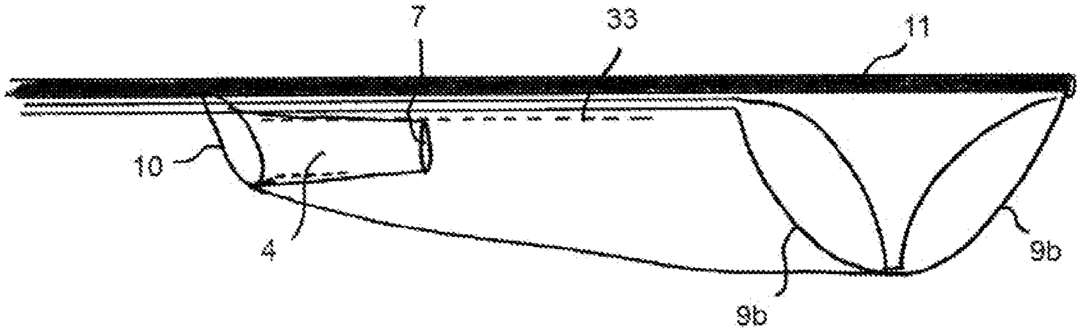

FIG. 12*c* describes a solution similar to FIG. 12*a* in which the distal port of the funnel 4 is a rigid ring 7.

Figure 12D:
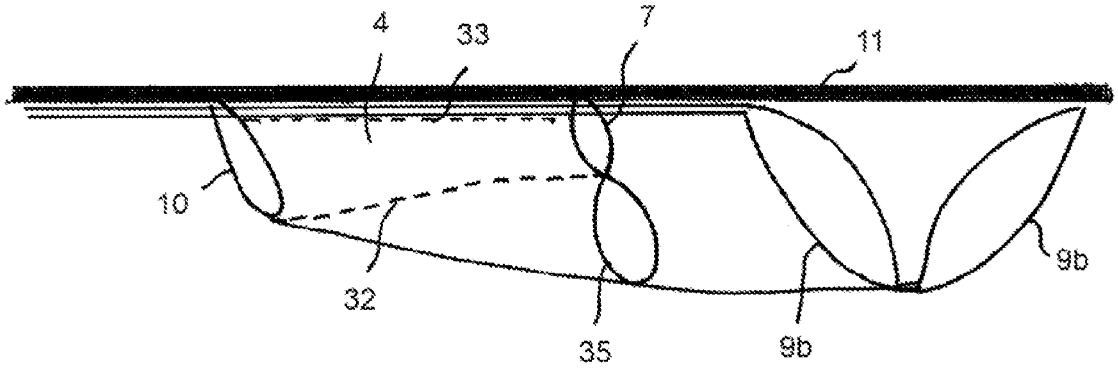

In the embodiment of FIG. 12*d*, the tubular filter 2 contains a "8" shape element made of two rigids rings, wherein the upper ring 7 forms the funnel 4 distal port and wherein the lower ring forms the basis of an emboli capturing intermediate structure 35.

The invention claimed is:

1. An intra-vessel transcatheter filter device configured to capture and remove emboli for preventing distal embolization, the device comprising:
- a tubular filter made of a flexible porous material, including a main body and a funnel,
- the main body having a length configured to extend within a vessel zone,
- the main body including
  - a distal end configured to be radially coupled with the vessel zone and hermetically sealed to the vessel zone when the device is in an active configuration, the distal end including a selectively actionable closure device so that the distal end is configured to open when the device is in the active configuration and close before a retraction of the device, and
  - a proximal end,
- the funnel forming an extension of the main body, with a base of the funnel located at the proximal end; and
- a support structure assembly including
  - a supporting catheter extending within the main body, the supporting catheter being a tubular body extending entirely through the main body from the proximal end to the distal end of the main body,
  - a radially expandable distal structure fixed to the distal end, and
  - a radially expandable proximal structure positioned in correspondence of the proximal end,
- wherein the supporting catheter is directly attached to the radially expandable distal structure and the radially expandable proximal structure.

2. The device according to claim 1, wherein the funnel has substantially a same cross-section area as the main body, the funnel being movable with respect to the main body between a first position in which a top of the funnel is positioned outside the main body and a second position in which the top of the funnel is positioned within the main body, between the distal end and the proximal end.

3. The device according to claim 1, wherein the funnel is fixed with respect to the main body, with a top of the funnel being positioned within the main body, between the distal end and the proximal end.

4. The device according to claim 1, wherein a porosity of the flexible porous material of the tubular filter is lower than 150 micron.

5. The device according to claim 1, wherein the proximal end is provided with a selectively actionable closure device.

6. The device according to claim 1, wherein the tubular filter is made of a low friction and flexible polymeric or composite material.

7. The device according to claim 1, wherein the tubular filter is coated with either a hydrophilic coating, low friction coating, or anti-thrombogenic coating or a combination thereof.

8. The device according to claim 1, wherein the radially expandable distal and proximal structures have a ring shape.

9. The device according to claim 8, wherein at least one of the radially expandable distal and proximal structures include two rings that are mutually joined.

10. The device according to claim 1, wherein an apex of the funnel includes a catheter access port, so that the funnel is configured to act as a conveyor for working catheters that cross the device.

11. The device according to claim 1, wherein the supporting catheter is configured to track inside relevant lumen other working catheters or instruments, whilst allowing emboli retaining.

12. The device according to claim 1, wherein the device has a geometry configured for intra-vessel procedures and length of the filter main body adapted to extend within a suitable vessel zone for intra-aortic procedures comprised between 10 cm and 30 cm to be adapted to extend from an ascending aorta to a descending aorta.

13. The device according to claim 1, further comprising: an artificial valve.

14. The device according to claim 1, further comprising: an intermediate structure including a dead end, the intermediate structure adapted to capture emboli transported by the blood flow.

15. The device according to claim 1, wherein the tubular filter comprises one or several stitching lines that define one or more specific areas, including the funnel, an intermediate structure including with a dead end, or a channel for the distal structure, or a combination thereof.

16. The device according to claim 1, wherein the porosity of the flexible porous mesh material of the tubular filter is between 40 microns and 70 microns.

17. A method for emboli protection during intra-vessel procedures, using the intra-vessel transcatheter filter device according to claim 1, the method comprising the steps of:

inserting via a suitable access the tubular filter and the support structure assembly collapsed into an external shaft and tracked along a guidewire;

positioning, by use of radiopaque markers and imaging technique, the distal end of the tubular filter at an intended position, for an intra-aortic procedure in an ascending aorta, upstream to an innominate artery;

proximally retrieving the external shaft to fully deploy the tubular filter from the distal to the proximal end, thus generally giving to the filter a configuration with two generally open ends, including the distal end sealing to a wall of the aorta, the proximal end acting as the base of the funnel;

enabling specific working instruments to enter inside the filter by crossing an apex of the funnel, with funnel and main body configured to prevent emboli downstream release; and enabling a selectively actionable closure device for the proximal end for the whole procedure and the selectively actionable closure device for the distal end before retrieving the tubular filter.

18. The device according to claim 1, wherein the supporting catheter is joined to the tubular filter.

19. The device according to claim 18, wherein the funnel is fixed with respect to the main body, with a top of the funnel being positioned within the main body, between the distal end and the proximal end.

* * * * *